US010286145B2

(12) United States Patent
Schabbach et al.

(10) Patent No.: US 10,286,145 B2
(45) Date of Patent: May 14, 2019

(54) DRIVE MECHANISM FOR A NEEDLE INSERTION ARRANGEMENT

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 217 days.

(21) Appl. No.: 14/916,674

(22) PCT Filed: Sep. 2, 2014

(86) PCT No.: PCT/EP2014/068596
§ 371 (c)(1),
(2) Date: Mar. 4, 2016

(87) PCT Pub. No.: WO2015/032742
PCT Pub. Date: Mar. 12, 2015

(65) Prior Publication Data
US 2016/0213839 A1 Jul. 28, 2016

(30) Foreign Application Priority Data

Sep. 5, 2013 (EP) .................................. 13183151

(51) Int. Cl.
*A61M 5/158* (2006.01)
(52) U.S. Cl.
CPC ..... *A61M 5/158* (2013.01); *A61M 2005/1585* (2013.01)

(58) Field of Classification Search
CPC .......... A61M 5/158; A61M 2005/1585; A61M 37/0076; A61M 37/0084; D05B 55/00;
(Continued)

(56) References Cited

U.S. PATENT DOCUMENTS

2005/0177201 A1* 8/2005 Freeman ............... A61N 1/0529
607/46
2007/0016129 A1* 1/2007 Liniger ................. A61M 5/158
604/93.01
(Continued)

FOREIGN PATENT DOCUMENTS

| CN | 102170928 | 8/2011 |
| DE | 10255133 | 4/2004 |

(Continued)

OTHER PUBLICATIONS

International Search Report and Written Opinion in International Application No. PCT/EP2014/068596, dated Oct. 1, 2014, 9 pages.
(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

The invention relates to a drive mechanism (9) for a needle insertion arrangement (1), the drive mechanism (9) comprising an actuator (5) coupled to a parallel linkage (10) adapted to convert a linear movement of the actuator (5) in a longitudinal direction (L) to a linear movement of a cross beam (7) in transverse direction (T) substantially at right angles with respect to the longitudinal direction (L).

17 Claims, 2 Drawing Sheets

(58) Field of Classification Search
CPC ........ D05B 55/02; D05B 55/04; D05B 55/06;
D05B 55/10; D05B 55/12; D05B 55/14;
D05B 55/16; A61B 90/10; A61B 90/11
See application file for complete search history.

(56) References Cited

U.S. PATENT DOCUMENTS

2014/0288511 A1\* 9/2014 Tan-Malecki ....... A61M 5/2466
604/244
2017/0156753 A1 6/2017 Deck et al.

FOREIGN PATENT DOCUMENTS

| EP | 1970091 | 9/2008 |
| EP | 2460553 | 6/2012 |
| JP | H11-303964 | 11/1999 |
| JP | 2006-527036 | 11/2006 |
| WO | WO 02/02165 | 1/2002 |
| WO | WO 2004/110527 | 12/2004 |

OTHER PUBLICATIONS

International Preliminary Report on Patentability in International Application No. PCT/EP22014/068596, dated Mar. 8, 2016, 7 pages.

\* cited by examiner

DRIVE MECHANISM FOR A NEEDLE INSERTION ARRANGEMENT

CROSS-REFERENCE TO RELATED APPLICATIONS

This application is a U.S. national stage application under 35 USC § 371 of International Application No. PCT/EP2014/068596, filed on Sep. 2, 2014, which claims priority to European Patent Application No. 13183151.3, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

EP 2 460 553 A1 discloses a device having a mounting formed of piston and connector movably mounted inside a body. A needle is secured to the mounting and a drive unit formed of propulsion unit, and spring drives the mounting toward an outer ring. The mounting is arranged so as to reach a position after activating the drive unit in which a distal surface of the mounting relative to a proximal end is more distant than contact area, where the device is arranged so as to enable a gradual passive return movement of the mounting once the position is reached.

There remains a need for an improved drive mechanism for a needle insertion arrangement.

SUMMARY OF THE INVENTION

Aspects of the present invention can provide an improved drive mechanism for a needle insertion arrangement.

The aspects can be implemented by a drive mechanism for a needle insertion arrangement according to claim 1.

Exemplary embodiments of the invention are given in the dependent claims.

According to the invention a drive mechanism for a needle insertion arrangement comprises an actuator coupled to a parallel linkage adapted to convert a linear movement of the actuator in a longitudinal direction to a linear movement of a cross beam in transverse direction substantially at right angles with respect to the longitudinal direction.

In an exemplary embodiment the linkage comprises a connecting rod coupled to the actuator.

In an exemplary embodiment the linkage comprises at least one cross beam.

In an exemplary embodiment the cross beam is arranged as a needle retainer arranged to retain an injection needle and to be moved between a retracted position and an extended position.

In an exemplary embodiment the linkage comprises at least two links, at least one of the links pivoted at one end in the connecting rod and at another end in a fixed anchor point, and at least another one of the links pivoted at one end in the cross beam and at another end in the connecting rod.

In an exemplary embodiment the linkage comprises at least four links, at least two of the links pivoted at one end in respective pivots in the connecting rod and at another end in respective pivots on fixed anchor points, and at least two others of the links pivoted at one end in respective pivots in the cross beam and at another end in respective pivots in the connecting rod.

In an exemplary embodiment the links pivoted in the fixed anchor points are arranged in parallel and wherein the links pivoted in the cross beam are arranged in parallel.

In an exemplary embodiment an imaginary line connecting the pivots in the fixed anchor points, the cross beam and the connecting rod are arranged in parallel.

In an exemplary embodiment the connecting rod comprises a transversal engagement bar for engaging a drive rod of the actuator in such a manner that a position of the drive rod relative the engagement bar is fixed with respect to movements in the longitudinal direction while the drive rod is allowed to slide along the engagement bar in the transverse direction.

In an exemplary embodiment the actuator is fixed in position relative the at least one pivot in the fixed anchor point.

In an exemplary embodiment the actuator is arranged as an electrical actuator.

In an exemplary embodiment of the electrical actuator is arranged as a piezo actuator.

In an exemplary embodiment the drive mechanism further comprises a linear guide for guiding the needle retainer in the transverse direction.

The drive mechanism may be applied in an insertion arrangement for moving an injection needle between a retracted position and an extended position, comprising a disposable unit, comprising a needle base, to which the needle is fixed, and the drive mechanism, wherein the needle retainer is adapted to retain the needle base.

The insertion arrangement has only limited space requirements determined by the required needle insertion depth thus allowing for low profile injection devices with a high wearing comfort. The insertion arrangement achieves high speed needle movements and exact needle guidance thus reducing pain for the patients when inserting and retracting the needle and increasing consumer acceptance and satisfaction. The insertion arrangement may be embodied with manual or motor powered operation. The low part count of the insertion arrangement and the low allows for an increased mechanical robustness and low manufacturing costs. The insertion arrangement is a fault-tolerant system.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
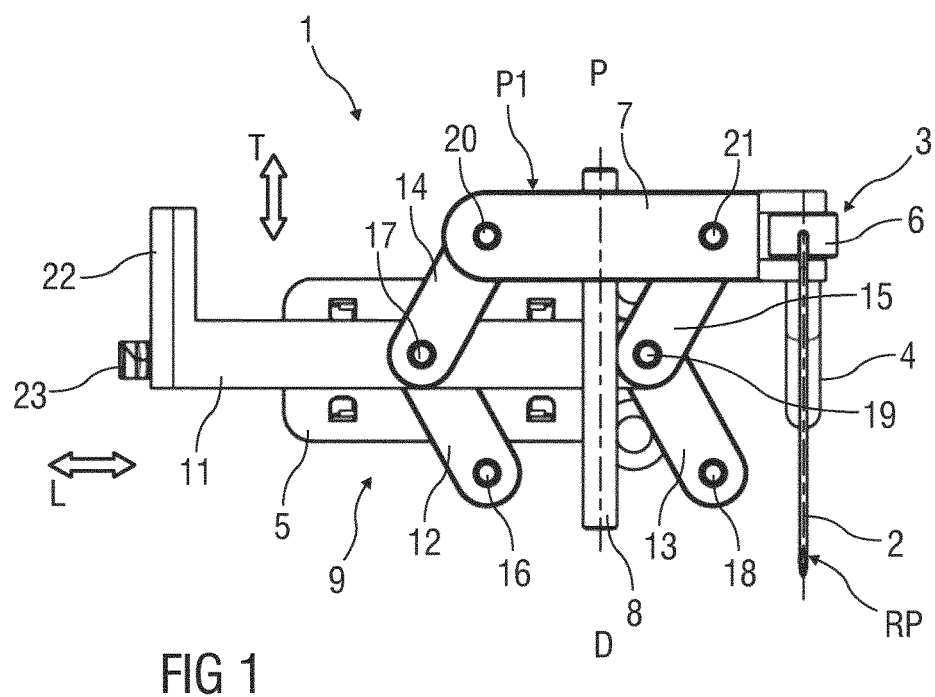
FIG. 1 is a schematic view of an exemplary embodiment of an insertion arrangement for inserting an injection needle into an injection site, wherein the needle is in a retracted position.

FIG. 1 is a schematic view of an exemplary embodiment of an insertion arrangement 1 for automatically or semi-automatically inserting an injection needle 2 into an injection site. The injection may be performed manually or by a motor. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a forked needle retainer 7 which is arranged to be moved between a retracted position RP and an extended position EP in a linear guide 8. This linear movement corresponds to insertion of the needle 2 into the injection site, e.g. subcutaneous body tissue and removal from the injection site, respectively.

A drive mechanism 9 for the needle 2 comprises an electrical actuator 5 such as a piezo actuator. Other types of actuators may be applied in alternative embodiments. In the illustrated embodiment the electrical actuator 5 is directly coupled to a linkage 10, e.g. a parallel linkage. In an alternative embodiment a gear may be arranged between the electrical actuator 5 and the linkage 10. The linkage 10 comprises a connecting rod 11 and four links 12, 13, 14, 15. A first link 12 is connected at one end to an anchor point in a case (not illustrated) by a first pivot 16 and at another end to the connecting rod 11 by a second pivot 17. A second link 13 is connected at one end to another anchor point in the case (not illustrated) by a third pivot 18 and at another end to the connecting rod 11 by a fourth pivot 19. A third link 14 is connected at one end to the needle retainer 7 by a fifth pivot 20 and at another end to the connecting rod 11 by the second pivot 17. A fourth link 15 is connected at one end to the needle retainer 7 by a sixth pivot 21 and at another end to the connecting rod 11 by the fourth pivot 19. Hence, the first pivot 16 and the third pivot 18 cannot move relative each other, the second pivot 17 and the fourth pivot 19 cannot move relative each other, and the fifth pivot 20 and the sixth pivot 21 cannot move relative each other. The first link 12 is arranged in parallel with the third link 14 and the second link 13 is arranged in parallel with the fourth link 15. The case (not illustrated) and the needle retainer 7 serve as cross beams in the linkage 10 and are arranged such that imaginary lines connecting the first pivot 16 with the third pivot 18, the second pivot 17 with the fourth pivot 19, and the fifth pivot 20 with the sixth pivot 21 are aligned in parallel. Due to this geometry of the linkage 10 linear movement of the connecting rod 11 in a longitudinal direction L results in a linear movement of the fifth pivot 20 relative the first pivot 16, and the sixth pivot 21 relative the third pivot 18 exclusively in a transverse direction T substantially at right angles with respect to the longitudinal direction L.

The connecting rod 11 comprises a transversal engagement bar 22 for engaging a drive rod 23 of the electrical actuator 5 in such a manner that a position of the drive rod 23 relative the engagement bar 22 is fixed with respect to movements in the longitudinal direction L while the drive rod 23 can slide along the engagement bar in the transverse direction T. The electrical actuator 5 can therefore be fixed in position relative the first and third pivot 16, 18 and remain engaged to the connecting rod 11 while allowing it to move in the transverse direction T.

A sequence of operation of the insertion arrangement 1 is as follows:

The insertion arrangement 1 is in an initial position as shown in FIG. 1. The disposable unit 3 with the needle base 6, the needle 2 and the tube 4 has been inserted in the forked needle retainer 7. The linkage 1 is in a first position P1, in which the needle retainer 7 is spaced from the connecting rod 11 thus keeping the needle 2 in a retracted position RP. In the first position P1 the first link 12 and the third link 14 are arranged at an obtuse angle relative each other. Likewise, the second link 13 and the fourth link 15 are arranged at an obtuse angle relative each other. In an alternative embodiment the first link 12 and the third link 14, and the second link 13 and the fourth link 15 could be arranged at a straight angle when in the first position P1 such that the first pivot 16, the second pivot 17 and the fifth pivot 20 are aligned and that the third pivot 18, the fourth pivot 19 and the sixth pivot 21 are aligned.

The electrical actuator 5 moves the connecting rod 11 in the longitudinal direction L away from the needle 2 thus rotating the links 12, 13, 14, 15 about their respective pivot 17, 19 in the connecting rod 11 reducing the angle between the first link 12 and the third link 14 and between the second link 13 and the fourth link 15, thereby also reducing the distance between the first pivot 16 and the fifth pivot 20 and between the third pivot 18 and the sixth pivot 21. The needle retainer 7 is thus moved out of the retracted position RP in a distal direction D.

Figure 2:
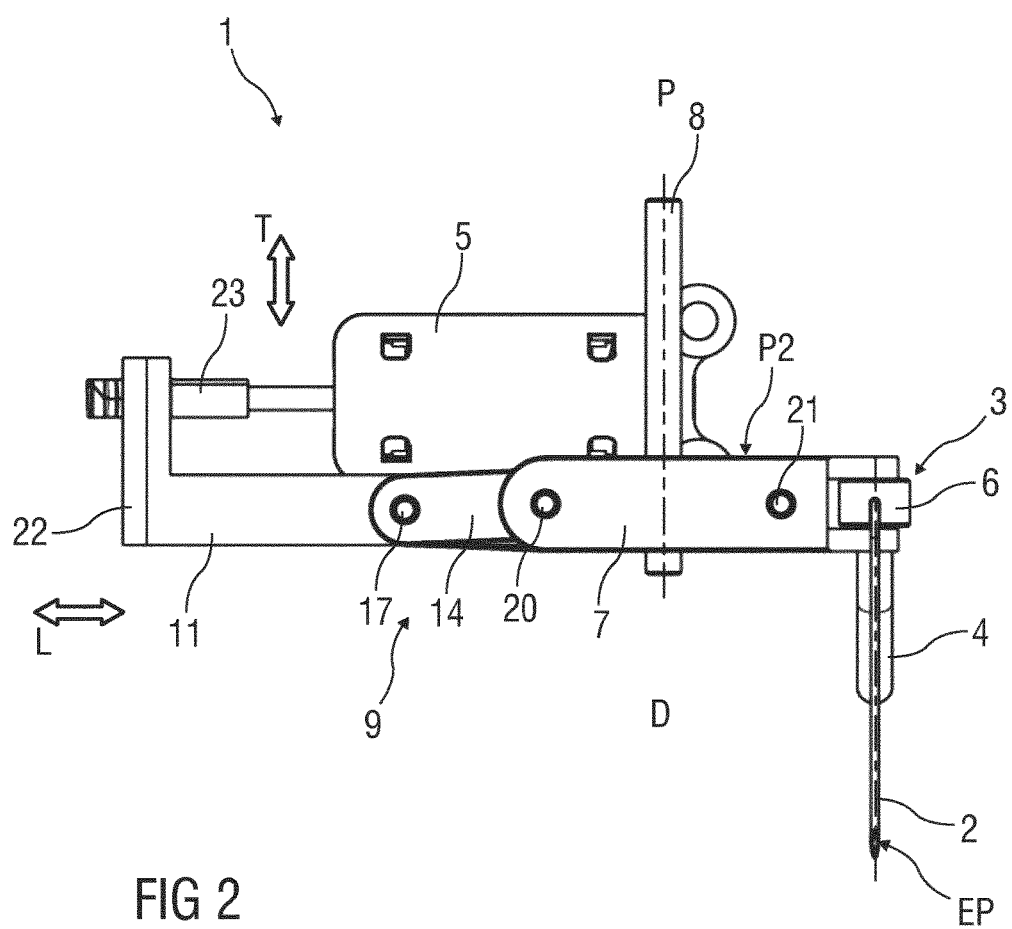
FIG. 2 is a schematic view of the insertion arrangement with the needle in an extended position.

FIG. 2 is a schematic view of the insertion arrangement 1 with the linkage 10 in a second position P2. The electrical actuator 5 has continued to move the connecting rod 11 thereby further reducing the angle between the first link 12 and the third link 14 and between the second link 13 and the fourth link 15. In the illustrated embodiment the angle is reduced to a very small value greater than 0°. Hence, the distance between the first pivot 16 and the fifth pivot 20 and between the third pivot 18 and the sixth pivot 21 is also reduced to a very small value greater than zero. The needle retainer 7 and the needle 2 are therefore fully advanced in the distal direction D into an extended position EP. The needle 2 may have reached its insertion depth in the injection site, e.g. subcutaneous body tissue.

In order to move the needle 2 from the extended position EP back into the retracted position RP the electrical actuator 5 would have to reverse its action, thereby moving the connecting rod 11 in the longitudinal direction L towards the needle 2, increasing the angle between the first link 12 and the third link 14 and between the second link 13 and the fourth link 15 until the linkage 10 arrives in the first position P1.

In an alternative embodiment the angle between the first link 12 and the third link 14 and between the second link 13 and the fourth link 15 in the second position P2 of the linkage 10 may be greater thus preventing the linkage 10 to get stuck in a dead centre.

In an alternative embodiment the linkage 10 could comprise only the connecting rod 11 and two links 12, 14 or 13, 15, one of them arranged between the connecting rod 11 and the anchor point in the case and the other arranged between the connecting rod 11 and the needle retainer 7. This embodiment could be improved by providing two linear guides 8 in parallel and connecting the link 14 or 15 to the needle retainer 7 between the two linear guides 8. Likewise, the linkage 10 could comprise more than two pairs of links 12, 13, 14, 15.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)
25, Asp28] Exendin-4(1-39)-NH2,
des Pro36, Pro37, Pro38 [Met(O)14, Trp(O2)25, Asp28]
Exendin-4(1-39)-(Lys)6-NH2,
H-(Lys)6-des Pro36, Pro37, Pro38 [Met(O)14, Trp(O2)25,
Asp28] Exendin-4(S1-39)-(Lys)6-NH2,
H-Asn-(Glu)5-des Pro36, Pro37, Pro38 [Met(O)14, Trp(O2)
25, Asp28] Exendin-4(1-39)-(Lys)6-NH2;
or a pharmaceutically acceptable salt or solvate of any one
of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

LIST OF REFERENCES 1 insertion arrangement
2 needle
3 disposable unit
4 tube
5 actuator
6 needle base
7 needle retainer
8 linear guide
9 drive mechanism 10 linkage
11 connecting rod
12 first link
13 second link
14 third link
15 fourth link
16 first pivot
17 second pivot
18 third pivot
19 fourth pivot
20 fifth pivot
21 sixth pivot
22 engagement bar
23 drive rod
D distal direction
EP extended position
L longitudinal direction
P proximal direction
P1 first position
P2 second position
RP retracted position
T transverse direction

The invention claimed is:

1. Drive mechanism for a needle insertion arrangement, the drive mechanism comprising:
   an actuator coupled to a parallel linkage adapted to convert a linear movement of the actuator in a longitudinal direction (L) to a linear movement of a cross beam in transverse direction (T) substantially at right angles with respect to the longitudinal direction (L), wherein the linkage comprises:
   a connecting rod coupled to the actuator, the connecting rod comprising a transversal engagement bar for engaging a drive rod of the actuator in such a manner that a position of the drive rod relative the engagement bar is fixed with respect to movements in the longitudinal direction (L) while the drive rod is allowed to slide along the engagement bar in the transverse direction (T);
   at least one cross beam; and
   at least two links, at least one of the links pivoted at one end in the connecting rod and at another end in a fixed anchor point, and at least another one of the links pivoted at one end in the cross beam and at another end in the connecting rod.

2. Drive mechanism according to claim 1, wherein the cross beam is arranged as a needle retainer arranged to retain an injection needle and to be moved between a retracted position (RP) and an extended position (EP).

3. Drive mechanism according to claim 2, further comprising a linear guide for guiding the needle retainer in the transverse direction (T).

4. Drive mechanism according to claim 1, wherein the linkage comprises at least four links, at least two of the at least four links pivoted at one end in respective pivots in the connecting rod and at another end in respective pivots on fixed anchor points, and at least two others of the at least four links pivoted at one end in respective pivots in the cross beam and at another end in respective pivots in the connecting rod.

5. Drive mechanism according to claim 4, wherein the links pivoted in the fixed anchor points are arranged in parallel and wherein the links pivoted in the cross beam are arranged in parallel.

6. Drive mechanism according to claim 4, wherein an imaginary line connecting the pivots in the fixed anchor points, the cross beam and the connecting rod are arranged in parallel.

7. Drive mechanism according to claim 1, wherein the actuator is fixed in position relative the at least one pivot in the fixed anchor point.

8. Drive mechanism according to claim 1, wherein the actuator is arranged as an electrical actuator.

9. Drive mechanism according to claim 8, wherein the electrical actuator is arranged as a piezo actuator.

10. Insertion arrangement for moving an injection needle between a retracted position (RP) and an extended position (EP), the insertion arrangement comprising:
    a disposable unit comprising a needle base to which the needle is fixed; and
    a drive mechanism comprising:
    an actuator coupled to a parallel linkage adapted to convert a linear movement of the actuator in a longitudinal direction (L) to a linear movement of a cross beam in transverse direction (T) substantially at right angles with respect to the longitudinal direction (L), wherein the linkage comprises:
    a connecting rod coupled to the actuator, the connecting rod comprising a transversal engagement bar for engaging a drive rod of the actuator in such a manner that a position of the drive rod relative the engagement bar is fixed with respect to movements in the longitudinal direction (L) while the drive rod is allowed to slide along the engagement bar in the transverse direction (T);
    at least one cross beam; and
    at least two links, at least one of the links pivoted at one end in the connecting rod and at another end in a fixed anchor point, and at least another one of the links pivoted at one end in the cross beam and at another end in the connecting rod,
    wherein a needle retainer is adapted to retain the needle base.

11. The insertion arrangement according to claim 10, wherein the cross beam is arranged as the needle retainer arranged to retain an injection needle and to be moved between a retracted position (RP) and an extended position (EP).

12. The insertion arrangement according to claim 11, the drive mechanism further comprising a linear guide for guiding the needle retainer in the transverse direction (T).

13. The insertion arrangement according to claim 10, wherein the linkage comprises at least four links, at least two of the at least four links pivoted at one end in respective pivots in the connecting rod and at another end in respective pivots on fixed anchor points, and at least two others of the at least four links pivoted at one end in respective pivots in the cross beam and at another end in respective pivots in the connecting rod.

14. The insertion arrangement according to claim 13, wherein the links pivoted in the fixed anchor points are arranged in parallel and wherein the links pivoted in the cross beam are arranged in parallel.

15. The insertion arrangement according to claim 13, wherein an imaginary line connecting the pivots in the fixed anchor points, the cross beam and the connecting rod are arranged in parallel.

16. The insertion arrangement according to claim 10, wherein the actuator is fixed in position relative the at least one pivot in the fixed anchor point.

17. The insertion arrangement according to claim 10, wherein the actuator is arranged as an electrical actuator.

\* \* \* \* \*